(12) United States Patent
Schwab et al.

(10) Patent No.: US 8,821,373 B2
(45) Date of Patent: Sep. 2, 2014

(54) DIRECTIONLESS (ORIENTATION INDEPENDENT) NEEDLE INJECTION PORT

(75) Inventors: Justin Schwab, Santa Barbara, CA (US); Sean Snow, Carpinteria, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 188 days.

(21) Appl. No.: 13/104,260

(22) Filed: May 10, 2011

(65) Prior Publication Data

US 2012/0289769 A1    Nov. 15, 2012

(51) Int. Cl.
*A61F 13/00* (2006.01)
*A61B 17/00* (2006.01)

(52) U.S. Cl.
USPC ............................................ 600/37; 606/157

(58) Field of Classification Search
USPC ......... 600/29–31, 37; 128/897–899, DIG. 25; 606/151, 157, 213, 228
See application file for complete search history.

(56) References Cited

U.S. PATENT DOCUMENTS

| | | |
|---|---|---|
| 586,113 A | 7/1897 | Bott |
| 2,163,048 A | 6/1939 | McKee |
| 2,737,954 A | 3/1956 | Knapp |
| 3,371,352 A | 3/1968 | Siposs et al. |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,840,018 A | 10/1974 | Heifetz |
| 3,958,562 A | 5/1976 | Hakim et al. |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Showell et al. |
| 4,161,943 A | 7/1979 | Nogier |
| 4,164,943 A | 8/1979 | Hill et al. |
| 4,190,040 A | 2/1980 | Schulte |
| 4,233,992 A | 11/1980 | Bisping |
| 4,265,252 A | 5/1981 | Chubbuck et al. |
| 4,280,722 A | 7/1981 | Guptil et al. |
| 4,413,985 A | 11/1983 | Wellner et al. |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.

(Continued)

*Primary Examiner* — John Lacyk
(74) *Attorney, Agent, or Firm* — Gordon & Jacobson, PC

(57) ABSTRACT

Generally described herein are certain embodiments directed to an orientation-independent injection port fluidly coupled to a gastric banding system. The injection port may be configured to simplify the port-targeting process when a medical professional attempts to penetrate the injection port with a needle during a gastric band-adjusting procedure. For example, the injection port may be orientation-independent with the entire outer shell acting as the needle access point. Alternatively, and/or in addition, the inner core of the injection port may be hard or firm, thereby allowing for easier locating (e.g., when the medical professional performs palpation). Furthermore, the hard inner core may prevent needle over-throws, and help stabilize pressure.

20 Claims, 5 Drawing Sheets

(56) References Cited

U.S. PATENT DOCUMENTS

| | | |
|---|---|---|
| 4,474,572 A | 10/1984 | McNaughton et al. |
| 4,502,335 A | 3/1985 | Wamstad et al. |
| 4,543,088 A | 9/1985 | Bootman et al. |
| 4,557,722 A | 12/1985 | Harris |
| 4,569,675 A | 2/1986 | Prosl et al. |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A | 6/1987 | Fenton, Jr. et al. |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A | 9/1988 | Wiita et al. |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A | 6/1989 | Hancock et al. |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A | 12/1989 | Johnston et al. |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,167,638 A | 12/1992 | Felix et al. |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A | 12/1997 | Flaherty et al. |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,270,475 B1 | 8/2001 | Bestetti et al. |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |

(56) References Cited

U.S. PATENT DOCUMENTS

| | | |
|---|---|---|
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze et al. |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon et al. |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,530,943 B2 | 5/2009 | Lechner |
| 7,553,298 B2 | 6/2009 | Hunt et al. |
| 7,561,916 B2 | 7/2009 | Hunt et al. |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum et al. |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,731,700 B1 | 6/2010 | Schytte |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 | 10/2010 | Birk et al. |
| 7,850,660 B2 | 12/2010 | Uth et al. |
| 7,862,546 B2 | 1/2011 | Conlon et al. |
| 7,909,754 B2 | 3/2011 | Hassler, Jr. et al. |
| 7,909,804 B2 | 3/2011 | Stats |
| 8,007,474 B2 | 8/2011 | Uth et al. |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyer |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon et al. |
| 2005/0131383 A1 | 6/2005 | Chen et al. |
| 2005/0148956 A1 | 7/2005 | Conlon et al. |
| 2005/0149143 A1 | 7/2005 | Libbus et al. |
| 2005/0209573 A1 | 9/2005 | Brugger et al. |
| 2005/0240155 A1 | 10/2005 | Conlon |
| 2005/0240156 A1 | 10/2005 | Conlon |
| 2005/0267500 A1 | 12/2005 | Hassler, Jr. et al. |
| 2005/0277899 A1 | 12/2005 | Conlon et al. |
| 2005/0283041 A1 | 12/2005 | Egle |
| 2005/0283118 A1 | 12/2005 | Uth et al. |
| 2005/0283119 A1 | 12/2005 | Uth et al. |
| 2006/0074439 A1 | 4/2006 | Garner et al. |
| 2006/0122578 A1 | 6/2006 | Lord et al. |
| 2006/0161186 A1 | 7/2006 | Hassler, Jr. et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk et al. |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1 | 9/2006 | Schulze et al. |
| 2006/0235445 A1 | 10/2006 | Birk et al. |
| 2006/0235448 A1 | 10/2006 | Roslin et al. |
| 2006/0247539 A1 | 11/2006 | Schugt et al. |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |
| 2007/0016231 A1 | 1/2007 | Jambor et al. |
| 2007/0027356 A1 | 2/2007 | Ortiz |
| 2007/0038255 A1 | 2/2007 | Kieval et al. |
| 2007/0060959 A1 | 3/2007 | Salo et al. |
| 2007/0073250 A1 | 3/2007 | Schneiter |
| 2007/0078391 A1 | 4/2007 | Wortley et al. |
| 2007/0088336 A1 | 4/2007 | Dalton |
| 2007/0088391 A1 | 4/2007 | McAlexander et al. |
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |

(56) References Cited

U.S. PATENT DOCUMENTS

| | | |
|---|---|---|
| 2007/0208313 A1 | 9/2007 | Conlon et al. |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe et al. |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin et al. |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| GB | 2192338 A | 1/1988 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/10667 | 2/2002 |

(56) References Cited

FOREIGN PATENT DOCUMENTS

| | | |
|---|---|---|
| WO | WO 02/74381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

DIRECTIONLESS (ORIENTATION INDEPENDENT) NEEDLE INJECTION PORT

FIELD

The present invention generally relates to medical systems and apparatus and uses thereof for treating obesity and/or obesity-related diseases, and specifically relates to injection ports penetrable by a needle to add or remove saline and/or other appropriate fill materials to a gastric banding system.

BACKGROUND

Adjustable gastric banding apparatus have provided an effective and substantially less invasive alternative to gastric bypass surgery and other conventional surgical weight loss procedures. Unlike gastric bypass procedures, gastric band apparatus implantations are reversible and require no permanent modification to the gastrointestinal tract. Moreover, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach may provide a feeling of satiety or fullness that discourages overeating. An example of a gastric banding system is disclosed in Roslin, et al., U.S. Patent Pub. No. 2006/0235448, the entire disclosure of which is incorporated herein by this specific reference.

Over time, a stoma created by a gastric band may need adjustment in order to maintain an appropriate size, which is neither too restrictive nor too passive. Accordingly, prior art gastric band systems provide a subcutaneous fluid injection port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

However, medical professionals frequently encounter difficulty with the process of targeting the injection port, including problems with locating the access port, determining the appropriate angle at which the needle should penetrate the access port, and determining whether the needle has sufficiently penetrated the access port.

Some attempts have been made to overcome these difficulties. For example, with reference to FIG. 1A, the Heliogast® EV3 implantantable port ("EV3 port") may allow needle penetration at a portion A of the EV3 port. However, the surface area of portion A constitutes only a fraction of the surface area of the entire outer surface of the EV3 port. In addition, the EV3 port still requires very precise needle insertion angles and locations such that they are in a discrete septum, as shown in FIG. 1B, and cannot facilitate a directionless or virtually directionless needle injection port, as shown in FIG. 1C. Indeed, FIG. 1C appears to illustrate that the EV3 port requires that needle insertions be orthogonal to the surface.

SUMMARY

This Summary is included to introduce, in an abbreviated form, various topics to be elaborated upon below in the Detailed Description.

In certain embodiments, it may be desirable to develop an injection port that is virtually or entirely orientation-independent such that the entire composite outer shell acts as a viable access point. By allowing needle penetration at various angles over a greater surface area of the injection port, such embodiments improve the process of targeting the injection port, among other benefits.

Generally described herein are certain embodiments directed to an orientation-independent injection port fluidly coupled to a gastric banding system, the injection port for simplifying the port-targeting process when a medical professional attempts to penetrate the injection port with a needle during a gastric band-adjusting procedure.

In one embodiment, the present invention is an injection port for the treatment of obesity or obesity-related diseases, the injection port implantable in a patient's body and fluidly coupled to tubing connected to an inflatable portion of a gastric band, the injection port comprising (1) an inner core made of a material to prevent a needle from penetrating the inner core, (2) an outer shell surrounding the inner core, and having a lower durometer than the inner core, the outer shell configured to allow penetration by the needle from any location on a surface of the outer shell and at any angle, and (3) a fluid conduit positioned between the inner core and the outer shell, the fluid conduit accessible by the needle to inject or remove fluid from the injection port of the gastric band.

In one embodiment, the injection port may be orientation independent with the entire outer shell or core acting as the needle access point. Alternatively, and/or in addition, the inner core of the injection port may be hard or firm (e.g., impenetrable by the needle), thereby allowing medical professionals to easily locate the injection port (e.g., when performing palpation). Furthermore, the hard inner core may prevent the needle from penetrating too deeply and exiting the injection port (e.g., preventing needle over-throws).

In one embodiment, a fluid conduit entirely or substantially encompasses the inner core. For example, the fluid conduit might not encompass the flange portion.

In one embodiment, the outer shell is concentric with the inner core.

In one embodiment, the outer surface of the inner core does not contact the inner surface of the outer shell.

In one embodiment, the outer shell may be a self-sealing membrane configured to be penetrable by a needle.

In one embodiment, the injection port may include internal features that allow fluid to flow when the outer shell or core of the injection port is under compression and/or when a vacuum is applied.

In one embodiment, the injection port may require less needle targeting when trying to penetrate the outer shell or core for saline removal/injection.

In one embodiment, the injection port may prevent pressure spikes (intentional or unintentional) from occurring due to volume occupation of the inner core.

In one embodiment, the injection port may be implanted without stitching during the implantation process.

BRIEF DESCRIPTION OF THE DRAWINGS

The features, obstacles, and advantages of the present invention will become more apparent from the detailed description set forth below when taken in conjunction with the drawings, wherein.

DETAILED DESCRIPTION

Apparatus, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

The present invention generally provides a directionless needle injection port having a hard inner core and a soft outer shell. The soft outer shell may be made from a needle penetrable and self-sealing material and may make available the entirety of its outer surface for needle penetration, replacing the need to target a restricted septum area of prior art ports, and thereby making the injection port easier to access when a medical professional needs to inject or remove fluids via the injection port.

While discussed herein as related to a gastric banding system, one skilled in the art will understand that the present invention is versatile and may be implemented with respect to any medical system, gastric-band related or not, which may be enhanced with a directionless needle injection port. For example, cancer patients who require an access port for frequent access to their veins may benefit from the implementation of an embodiment of a directionless injection port as described herein.

Figure 1A:
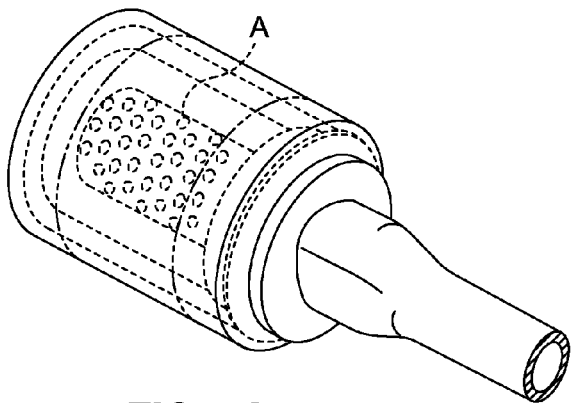
FIG. 1A illustrates a prior art injection port.
Figure 1B:
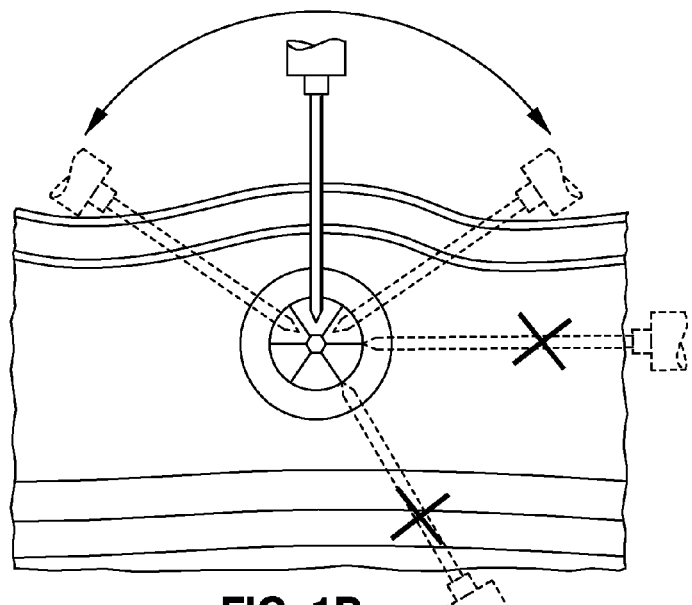
FIG. 1B illustrates the access locations of the injection port of FIG. 1A.
Figure 1C:
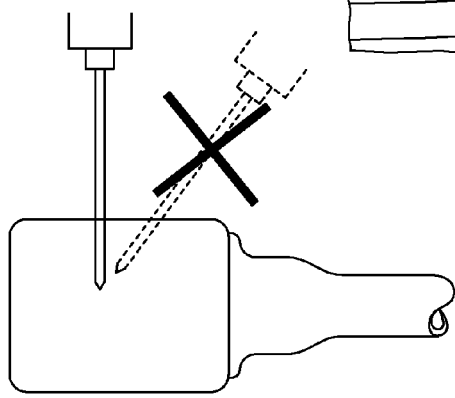
FIG. 1C illustrates the allowable and non-allowable access angles of the injection port of FIG. 1A.
Figure 2:
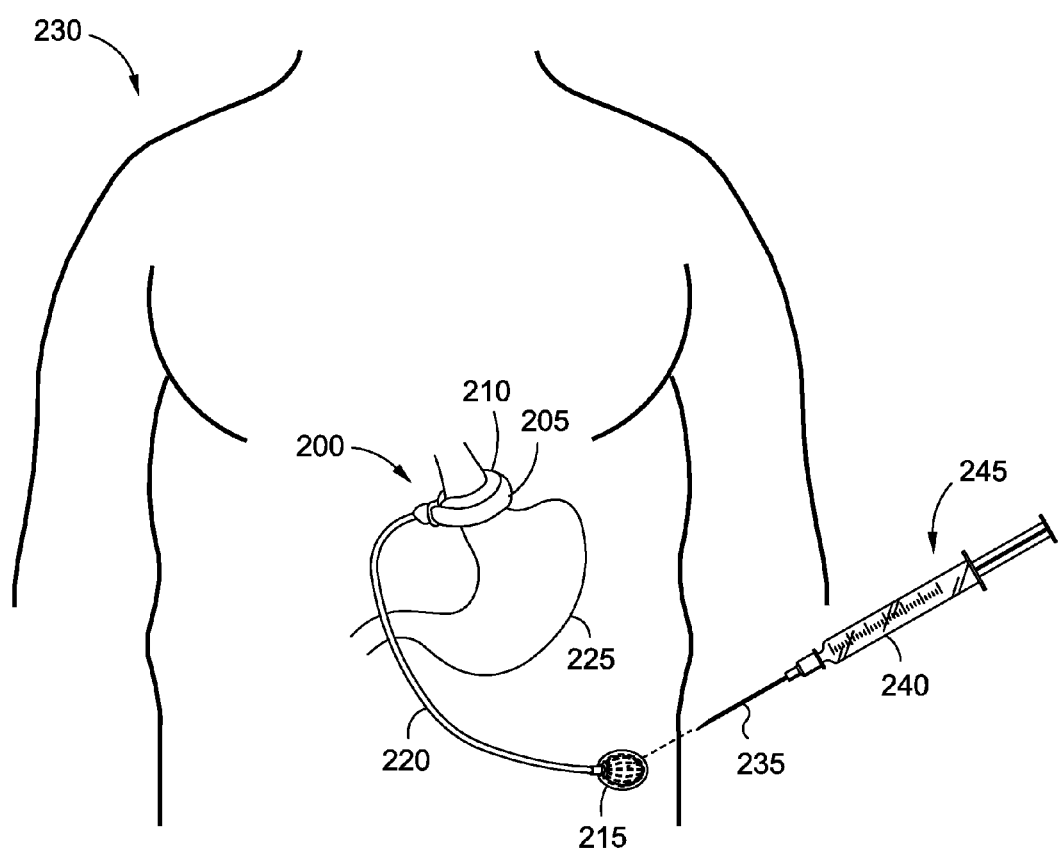
FIG. 2 illustrates a perspective view of a gastric banding system according to an embodiment of the present invention.

Turning to FIG. 2, an implanted gastric banding system 200 is illustrated as implanted within a patient's body 230, and more specifically, forming a stoma around an upper region of a stomach 225 of the patient's body 230. The gastric banding system 200 may include a gastric band 205 having an inflatable portion 210. The gastric band 205 may be fluidly coupled with an injection port 215 via a tubing 220. A fluid injection device 245 may include a syringe 240 and a needle 235 which may penetrate the patient's body 230 at a location proximal to the injection port 215 to add or remove fluid. The fluid added or removed may either inflate (if fluid is added) or deflate (if fluid is removed) the inflatable portion 210 of the gastric band 205, thereby increasing (if fluid is added) the degree of constriction that the gastric band 205 imparts on the upper region of the stomach 225 or decreasing (if fluid is removed) the degree of constriction that the gastric band 205 imparts on the upper region of the stomach 225. In this manner, adjustments to the gastric banding system 200 may be performed via the injection port 215.

Figure 3A:
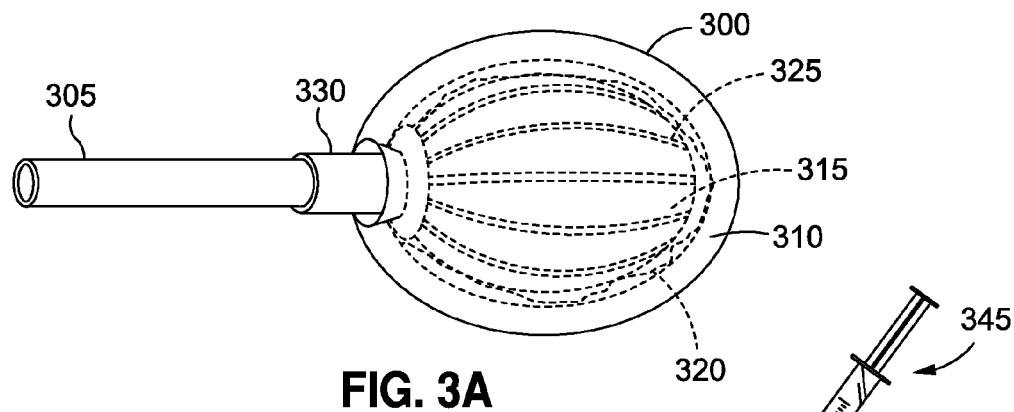
FIG. 3A illustrates a perspective view of a directionless needle injection port according to an embodiment of the present invention.

FIG. 3A is an injection port 300 attached to a tubing 305. In one embodiment, the injection port 300 may be the injection port 215 of FIG. 2, and the tubing 305 may be the tubing 220 of FIG. 2. The rest of the gastric banding system has been omitted for clarity. The injection port 300 may include an outer shell 310 and an inner core 315. A fluid conduit 320 may be formed between an inner surface 311 of the outer shell 310 and an outer surface 316 of the inner core 315. In one embodiment, the fluid conduit 320 may be the entire spatial gap between the inner surface 311 of the outer shell 310 and the outer surface 316 of the inner core 315. The inner core 315 may further include channels 325 for fluid flow. The channels 325 may be grooves or indentations formed on the outer surface 316 of the inner core 315 to improve fluid flow. In addition, the injection port 300 may include an attachment flange 330 to prevent the fluid from leaking out of the fluid conduit 320 and to hold the tubing 305 in place at the location where the tubing 305 is coupled to the injection port 300.

As shown, the fluid conduit 320 wraps around virtually the entire outer surface 316 of the inner core 315, thereby allowing a medical professional access to the fluid conduit 320 by inserting a needle (e.g., the needle 335) virtually anywhere and at any angle on the outer shell 310. In this manner, the medical professional may be able to add or remove fluid via the injection port 300 without regard to the orientation or direction that the injection port 300 is facing. Accordingly, the injection port 300 may be deemed orientation-less and/or direction-less. In one embodiment, the outer surface 316 of the inner core 315 does not contact the inner surface 311 of the outer shell 310 thereby forming the fluid conduit 320.

The outer shell 310 may be constructed out of a soft plastic, polymer or other material penetrable by a needle since the outer shell 310 is designed to be punctured by a needle (e.g., the needle 235) to allow for the addition or removal of fluid. In addition, the soft plastic, polymer or other material used to construct the outer shell 310 may have self-sealing characteristics as it may be desirable to allow the outer shell 310 to withstand repeated, periodic insertion and withdrawal of needles. The outer shell 310 may be shaped as an ellipsoid or an "olive", but other geometric configurations may be possible such as a sphere, etc.

In one embodiment, the outer shell 310 may be a membrane having a characteristic of being penetrable by a needle to allow for fluid addition or removal to the injection port 300 while acting as a barrier to prevent the leakage of the fluid from within the injection port 300 (i.e., the fluid conduit 320).

In one embodiment, the outer shell 310 may have a composite build and may incorporate a micro-mesh to allow for leak-free needle insertions and removals. The entire outer surface of the outer shell 310 may also be loosely covered in a polypropylene bio-integrating mesh to allow for stitch-free implantation, thereby reducing procedural complexity and duration.

In addition to and/or alternatively, other materials of low durometer may be used. The outer shell 310 may also be designed such that a medical professional, in performing palpation with his or her fingers, may be able to locate the injection port 300 by feeling the inner core 315 (which is hard) through the outer shell 310 (which is soft).

Once the needle (e.g., the needle 335) is inserted through the outer shell 310, the inner core 315 may prevent the needle (e.g., the needle 335) from unintentionally overshooting (and/or unintentionally exiting) the fluid conduit 320, as the inner core 315 is constructed out of a relatively high durometer plastic core, titanium, stainless steel, composite ceramics, and/or other suitable material, configured to withstand and/or prevent needle penetration. In one embodiment, the durometer of the inner core 315 is greater than the durometer of the outer shell 310.

Figure 3B:
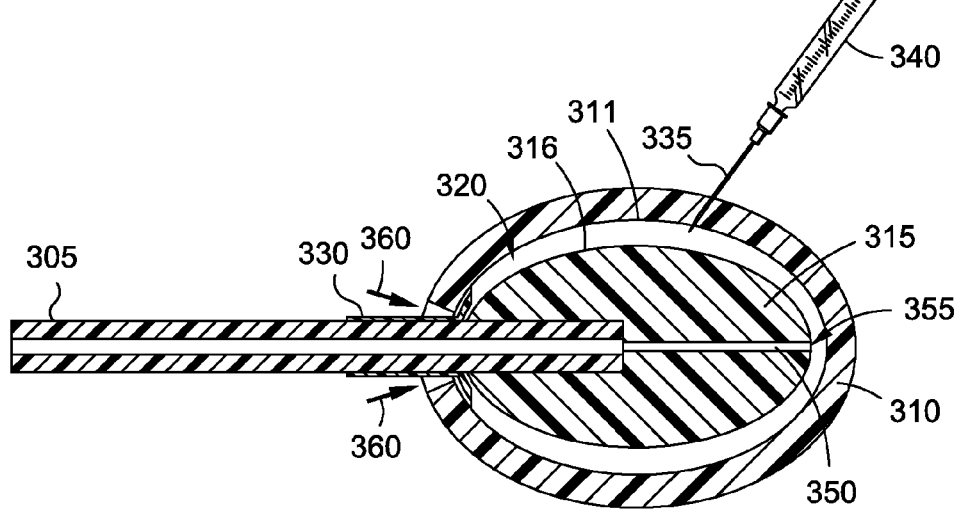
FIG. 3B illustrates a cross-sectional view of a directionless needle injection port according to an embodiment of the present invention.

FIG. 3B is a cross-sectional view of the injection port 300 illustrating the operation of the injection port 300. Also shown is a fluid injection device 345 which may include a syringe 340 and a needle 335. The needle 335 may penetrate the outer shell 310 before being stopped by the inner core 315. The stoppage of the needle 335 by the inner core 315 serves to ensure that the needle 335 is correctly inserted because if the needle 335 has reached the outside surface 316 of the inner core 315, the needle 335 is necessarily at a location configured to access the fluid conduit 320. Accordingly, the medical professional need not guess whether the needle 335 is correctly inserted. Once positioned, the needle 335 may be utilized to access the fluid conduit 320 to add or remove fluid from the injection port 300. As shown, the fluid conduit 320 may be in fluid communication with the tubing 305 via a fluid conduit-tubing connection path 350 at an opening 355. In this manner, fluid communication between the injection port 300 and the rest of the gastric banding system (not shown) is achieved via the tubing 305.

The fluid within the fluid conduit 320 is prevented from leaking out of the gastric banding system (e.g., the gastric banding system 200) by the attachment flange 330. The attachment flange 330 may be constructed out of a fluid-impenetrable material and may include a cylindrical portion which attaches to the outside of the tubing 305 and a flange portion which attaches to the inside surface 311 of the outer shell 310. In this manner, fluid within the fluid conduit 320 is prevented from exiting or leaking out of the injection port at a location designated by arrows 360. The attachment flange 330 may further provide strain relief for the injection port 300. The tubing 305 is connected to and inserted into the inner core 315. The tubing 305 and/or the attachment flange 330 are used to hold the inner core 315 in place within the outer shell 310.

Figure 3C:
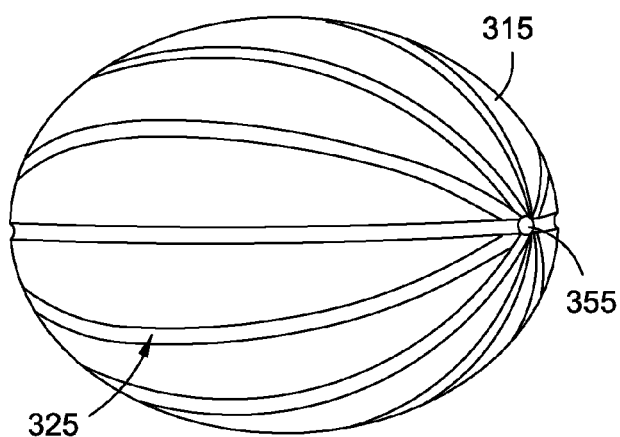
FIG. 3C illustrates a close-up view of an inner core of a directionless needle injection port according to an embodiment of the present invention.

FIG. 3C illustrates the inner core 315 with the outer shell (e.g., the outer shell 310) omitted for clarity. As shown, the inner core 315 may be shaped as an ellipsoid or an "olive", but other geometric configurations may be possible such as a sphere, etc. The inner core 315 may include channels 325 spaced apart extending from one end of the inner core 315 to another, and culminating at the opening 355, which may be an interface to a lumen (e.g., the fluid conduit-tubing connection path 350) for fluid flow between the injection port 300 and the rest of the gastric banding system (not shown). As shown, all the channels 325 may be spaced apart from one another but may converge at the ends and come into contact with one another at single end points such as at the opening 325. The channels 325 allow the fluid to converge at the opening 325 to better and more easily flow into and out of the path 350.

In one embodiment, the geometry of the channels 325 may be configured to optimize the overall volume of the fluid conduit 320. For example, deeper and/or wider channels 325 may increase the overall volume capabilities of the fluid conduit 320, whereas shallower and/or narrower channels 325 may decrease the overall volume capabilities of the fluid conduit 320. Similarly, the lumen (e.g., the fluid conduit-tubing connection path 350) may be configured and sized to support a larger volume of fluid or a smaller volume of fluid.

In one embodiment, additional lumens may be included to provide additional conduits between the access or injection port 300 and the inflatable portion (e.g., the inflatable portion 210) of the gastric band (e.g., the gastric band 205).

In one embodiment, the inner core 315 may be further modified to include any of a number of features. For example, pressure relief holes (not shown) may be beneficial in a situation where one side of the outer shell (e.g., the outer shell 310) is under compression, thereby allowing fluid to still flow to the opening 340. Alternatively, non-smooth geometry may provide better tactile feedback to the medical professional when the needle (e.g., the needle 335) penetrates the outer shell (e.g., the outer shell 310).

In one embodiment, the inner core 315 may have multiple functionalities. For example, the inner core 315 may prevent needle overthrows by offering a hard surface impenetrable by the needle 335. Also, the inner core 315 may enhance patient safety and discomfort by limiting unintentional pressure spikes. By preventing the injection port from collapsing, unintentional constriction by the inflatable portion (e.g., the inflatable portion 210) of the gastric band (e.g., the gastric band 205) may be stopped. Furthermore, the mass and/or hardness of the inner core 315 may enable medical professionals to more easily locate the injection port 300 under the patient's skin.

In one embodiment, a fluid conduit (e.g., the fluid conduit 320) may entirely or substantially encompasses the inner core 315. For example, the fluid conduit 320 might not encompass the attachment flange 360.

In one embodiment, the outer shell 310 is positioned concentric with the inner core 315.

Figure 4A:
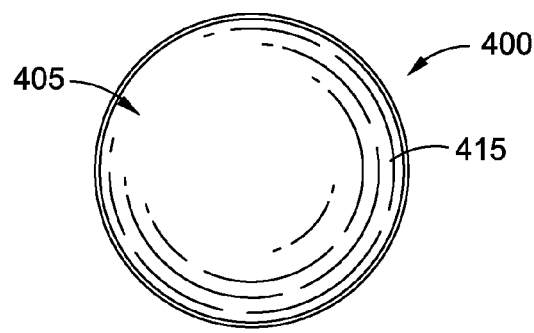
FIG. 4A illustrates a top view of an inner core of a directionless needle injection port according to an embodiment of the present invention.
Figure 4B:
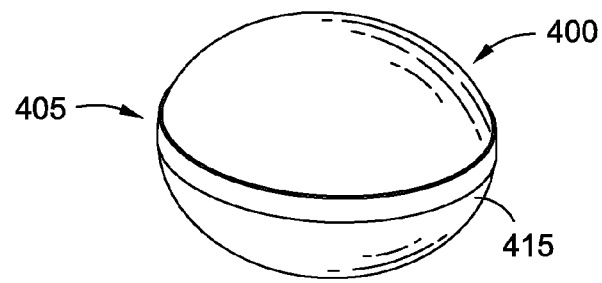
FIG. 4B illustrates a perspective view of an inner core of a directionless needle injection port according to an embodiment of the present invention.

FIGS. 4A and 4B illustrate a top view and a side perspective view, respectively, of one embodiment of an inner core 415. Here, the other portions of the gastric banding system including the tubing have been omitted for clarity. In addition, certain parts of an injection port 400 such as the outer shell and/or the attachment flange have also been omitted for clarity. In this embodiment, the inner core 415 may be flattened, thereby providing the benefit of flip-resistance immediately after the implantation procedure. As shown, the inner core 415 may have a smooth surface.

Figure 5:
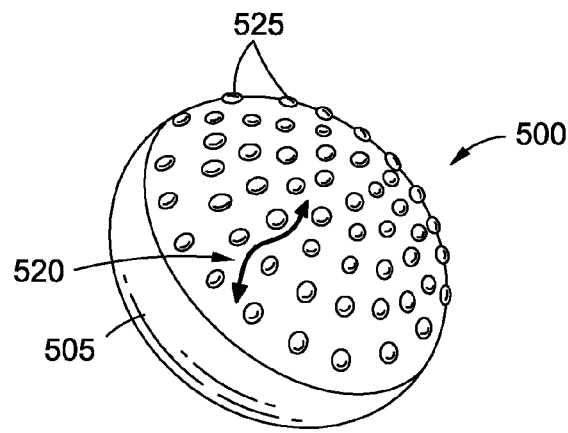
FIG. 5 illustrates a perspective view of an inner core of a directionless needle injection port according to an embodiment of the present invention.

FIG. 5 illustrates another embodiment of an inner core 515. Again, for clarity, the other portions of the gastric banding system, and certain parts of an injection port 500 have been omitted for clarity. However, as shown, the inner core 515 may include alternative fluid channels created by protrusions 525 (e.g., formed in the shape of circles or ovals) which allow fluid flow and pressurization of the fluid layer during a needle penetration procedure while the outer shell (not shown) is compressed over the inner core 515. Arrow 520 illustrates an example of one such fluid channel that the fluid may take along the exterior of the inner core 515. In addition, the protrusions 525 may prevent an outer shell (not shown) from collapsing against the inner core 515 during vacuum. The size and spacing of the protrusions 525 may be designed to allow for more efficient fluid flow. For example, in one embodiment, the protrusions 525 may be unevenly spaced apart and have varying heights and diameters. In another embodiment, the protrusions 525 may have uniform spacing, heights and diameters.

Figure 6:
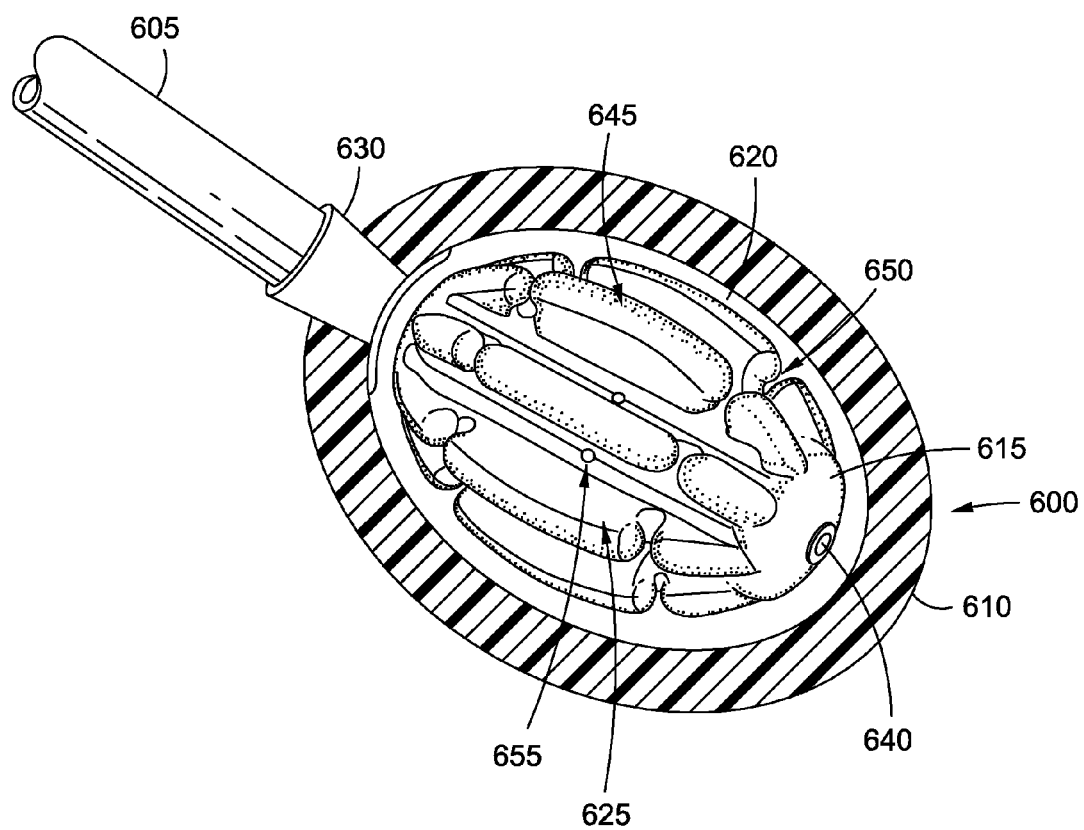
FIG. 6 illustrates a perspective view of a directionless needle injection port according to an embodiment of the present invention.

FIG. 6 illustrates an embodiment of an injection port 600. In one embodiment, an injection port 600 may be the injection port 215 of FIG. 2 and a tubing 605 may be the tubing 220 of FIG. 2. The rest of the gastric banding system has been omitted for clarity. As shown, the injection port 600 may include an outer shell 610 surrounding virtually the entirety of an inner core 615. A fluid conduit 620 may be formed between an inner surface of the outer shell 610 and an outer surface of the inner core 615. The inner core 615 may further include ridges 645 having ridge interruptions 650.

As shown, the ridges 645 may be oriented longitudinally about the exterior of the inner core 615, and may form channels 625 between adjacent ridges 645 for fluid flow. The ridges 645 may be multi-functional. For example, in addition to forming the channels 625 for fluid flow (e.g., which may occur when the fluid volume is under vacuum, such as when the medical professional is removing fluid from the injection port 600), the ridges 645 may further provide exaggerated needle-stopping structures to prevent needle over-throws when the medical professional is attempting to insert a needle (e.g., the needle 235) into the fluid conduit 620. In one embodiment, the ridges 645 and the rest of the inner core 615 may be constructed out of a relatively high durometer plastic core configured to withstand and/or prevent a needle (e.g., the needle 235) from puncturing through. The one or more ridge interruptions 650 on each ridge 645 may provide for fluid flow circumferentially to ensure volume and/or pressure stability when portions of the injection port 600 are collapsed (e.g., when the patient is in a sitting position, a portion of the injection port 600 may be compressed on one side).

The channels 625 may include one or more fluid holes 655 between the ridges 645 which allow for fluid communication between the injection port 600 and the gastric band (not shown) via the tubing 605 even when the injection port 600 is under compression or a vacuum. In addition, the channels 625 may allow for easier fluid travel to and from an opening 640 (which is configured to fluidly couple the injection port 600 to the rest of the gastric banding system).

In addition, the injection port 600 may include an attachment flange 630 to prevent fluid from leaking out of the fluid conduit 620 and to hold the tubing 605 in place at the location where the tubing 605 is coupled to the injection port 600.

Similar to the injection port 300 of FIG. 3, the fluid conduit 620 may wrap around virtually the entire surface of the inner core 615 including the ridges 645, thereby allowing a medical professional to access the fluid conduit 620 by inserting a needle (e.g., the needle 235) virtually anywhere and at any angle on the outer shell 610. In this manner, the medical professional may be able to add or remove fluid via the injection port 600 without regard to the orientation or direction that the injection port 600 is facing. Accordingly, the injection port 600 may be deemed orientation-less and/or direction-less.

In addition, as the outer shell 610 is designed to be punctured by a needle (e.g., needle 235), the outer shell 610 may be constructed out of a soft plastic and may, in one embodiment, have a composite build and incorporate a micro-mesh to allow for leak-free needle insertions and removals. The entire outer surface of the outer shell 610 may also be loosely covered in a polypropylene bio-integrating mesh to allow for stitch-free implantation, thereby reducing procedural complexity and duration.

In addition and/or alternatively, other materials of low durometer may be used. The outer shell 610 may also be designed such that a medical professional in performing palpation with his or her fingers may be able to locate the injection port 600 by feeling the ridges 645 of the inner core 615 through the outer shell 610.

Unless otherwise indicated, all numbers expressing quantities of ingredients, volumes of fluids, and so forth as used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An injection port for the treatment of obesity or obesity-related diseases, the injection port implantable in a patient's body and fluidly coupled to tubing connected to an inflatable portion of a gastric band, the injection port comprising:
    an inner core made of a material to prevent a needle from penetrating the inner core;
    an outer shell surrounding the inner core, and having a lower durometer than the inner core; and
    a fluid conduit formed between the inner core and the outer shell, wherein the outer shell is configured to allow penetration by the needle from any location on a surface of the outer shell and at any angle into the fluid conduit to inject fluid to or remove the fluid from the inflatable portion of the gastric band.

2. The injection port of claim 1 wherein the inner core further includes a lumen extending longitudinally through an interior of the inner core, the lumen extending through the interior of the inner core for connecting to the tubing, and allowing fluid to pass from the fluid conduit to the tubing.

3. The injection port of claim 1 wherein the inner core further includes a channel on the outside surface of the inner core for enhancing the fluid transfer between the needle and the opening.

4. The injection port of claim 1 further comprising an attachment flange configured to improve flexibility of the injection port, the attachment flange having a cylindrical portion for attaching to the tubing and providing strain relief and a flange portion for preventing fluid from leaking out of the fluid conduit.

5. The injection port of claim 1 wherein the outer shell is composed of a plastic and the inner core is composed of a material selected from a group consisting of a plastic, a titanium metal, a stainless steel, a composite ceramic, and combinations thereof.

6. The injection port of claim 1 wherein the outer shell further includes a bio-integrating mesh on an outside surface.

7. The injection port of claim 1 wherein the fluid conduit is defined by an outer surface of the inner core and an inner surface of the outer shell.

8. An injection port for the treatment of obesity or obesity-related diseases, the injection port implantable in a patient's body and fluidly coupled to tubing connected to an inflatable portion of a gastric band, the injection port comprising:
    an olive-shaped inner core made of a material selected from a group consisting of a plastic, a titanium metal, a stainless steel, a composite ceramic, and combinations thereof, the inner core configured to prevent a needle from penetrating an outside surface of the inner core; and
    an olive-shaped outer shell surrounding the inner core, and having a lower durometer than the inner core, the outer shell configured to allow penetration by a needle from any location on a surface of the outer shell and at any angle; and
    a fluid conduit defined by an outer surface of the inner core and an inner surface of the outer shell, the fluid conduit accessible by the needle to inject fluid to or remove the fluid from the inflatable portion of the gastric band.

9. The injection port of claim 8 wherein the inner core has a substantially smooth outer surface.

10. The injection port of claim 8 wherein the inner core is substantially flattened such that a longitudinal length of the inner core is greater than a thickness of the inner core.

11. The injection port of claim 8 wherein the inner core has a plurality of protrusions on the outer surface, the protrusions defining a plurality of fluid paths.

12. The injection port of claim 8 wherein the inner core has a plurality of longitudinally extending ridges, the ridges defining a plurality of fluid paths.

13. The injection port of claim 12 wherein each of the plurality of ridges comprises a ridge interruption forming a gap within the ridge.

14. The injection port of claim 12 wherein the ridges further define a plurality of parallel fluid channels.

15. The injection port of claim 14 wherein at least one fluid channel includes a hole for fluid communication with the tubing.

16. The injection port of claim 8 further comprising an attachment flange having a cylindrical portion for attaching to the tubing and a flange portion for preventing fluid from leaking out of the fluid conduit.

17. The injection port of claim 8 wherein the outer shell further includes a bio-integrating mesh on an outside surface.

18. The injection port of claim 8 wherein the fluid conduit is defined by an outer surface of the inner core and an inner surface of the outer shell.

19. The injection port of claim 8 wherein the inner core further includes a lumen extending longitudinally through an interior of the inner core, the lumen extending through the interior of the inner core for connecting to the tubing, and allowing fluid to pass from the fluid conduit to the tubing.

20. An implantable gastric banding system for the treatment of obesity or obesity-related diseases, the gastric banding system disposed within a patient's body, the gastric banding system comprising:
    a gastric band having a ring and an inflatable portion, the inflatable portion of the gastric band for constricting an upper stomach of the patient;
    a tubing fluidly coupled to the inflatable portion of the gastric band; and
    an injection port fluidly coupled to the tubing and the inflatable portion of the gastric band, the injection port including:
        an olive-shaped inner core composed of a plastic configured to prevent a needle from penetrating the inner core,
        an olive-shaped outer shell surrounding the inner core, and having a lower durometer than the inner core, the outer shell configured to allow penetration by the needle from any location on a surface of the outer shell and at any angle, and
        a fluid conduit formed between the inner core and the outer shell, the fluid conduit accessible by the needle to inject fluid to or remove the fluid from the injection port of the gastric band, the fluid conduit fluidly coupled to the inflatable portion of the gastric band via the tubing.

* * * * *